United States Patent [19]

Kondo et al.

[11] Patent Number: 5,024,973
[45] Date of Patent: Jun. 18, 1991

[54] CRYSTALLIZED GLASS TOOTH CROWN MATERIAL

[75] Inventors: Kazuo Kondo; Masahiko Okuyama, both of Aichi, Japan

[73] Assignee: NGK Spark Plug Co., Ltd., Aichi, Japan

[21] Appl. No.: 943,828

[22] Filed: Dec. 17, 1986

Related U.S. Application Data

[63] Continuation of Ser. No. 719,103, Apr. 2, 1985, abandoned.

[30] Foreign Application Priority Data

Apr. 2, 1984 [JP] Japan .................................. 59-65531

[51] Int. Cl.$^5$ .............................................. C03C 10/02
[52] U.S. Cl. ....................................................... 501/10

[56] References Cited

U.S. PATENT DOCUMENTS

| | | | |
|---|---|---|---|
| 3,519,445 | 7/1970 | MacDowell et al. | 501/10 |
| 3,751,272 | 8/1973 | Izumitani et al. | 501/46 |
| 3,785,835 | 1/1974 | Izumitani et al. | 501/48 |
| 3,940,255 | 2/1976 | Harrington et al. | 65/33 |
| 4,141,738 | 2/1979 | Rapp | 501/10 |
| 4,202,700 | 5/1980 | Wilder, Jr. | 501/48 |
| 4,309,485 | 1/1982 | Kondo et al. | 428/457 |

FOREIGN PATENT DOCUMENTS 1174475 12/1969 United Kingdom ............... 501/10

*Primary Examiner*—Ferris H. Lander
*Attorney, Agent, or Firm*—Sughrue, Mion, Zinn, Macpeak & Seas

[57] ABSTRACT

A crystallized glass tooth crown is described, consisting essentially of from 40 to 75 mol % component X, from 20 to 55 mol % component Y and from 0.1 to 10 mol % component Z, wherein component X is $P_2O_5$, component Y is selected from ZnO, $K_2O$, $B_2O_3$ and $Al_2O_3$ in an amount of up to 20 mol % and additionally CaO and BaO in an amount to bring the total mol % of component y to up to 55 mol %, and component Z is selected from SrO, $Ta_2O_5$, $La_2O_3$, $CeO_2$ and $Nb_2O_5$.

This tooth crown and is superior in chemical resistance, has a good appearance, and has almost the same mechanical strength and hardness as those of the enamel of the human teeth.

A process for producing crystallized glass tooth crown is also described.

7 Claims, No Drawings

CRYSTALLIZED GLASS TOOTH CROWN MATERIAL

This is a continuation of application Ser. No. 719,103, filed Apr. 2, 1985, and now abandoned.

FIELD OF THE INVENTION

The present invention relates to a crystallized glass tooth crown material.

BACKGROUND OF THE INVENTION

Materials for use in living bodies, e.g., in prosthesis, redintegration, correction, etc., in the field of dentistry have conventionally been made of metals, such as alloys of one or more of Cr, Fe, Co, Ni, Cu, Zn, Be, Cd, and Au. These metals excusive of Au are also typically somewhat deficient in chemical resistance. Thus there is some tendency for oxidation and discoloration to occur during the storage or use, and, furthermore, there is a possibility of the metals exerting adverse influences on the living body. Au is very expensive. Further, the materials for use in living bodies have been made of plastics, composites containing resin and inorganic filler, or inorganic ceramics. However, the plastics lack in an affinity for living body, the composites are easy to discolor and exert adverse influences on the living body, and the ceramics are difficult to be applied to tooth crown materials due to their shrinking during sintering.

SUMMARY OF THE INVENTION

An object of the present invention is to provide a crystallized glass tooth crown material which is superior in chemical resistance, particularly water resistance, has a good appearance and has almost the same mechanical strength and hardness as those of the enamel of the human teeth.

Based on extensive investigations, a material satisfying the object of the present invention has now been found, viz., a crystallized glass tooth crown material consisting essentially of from 40 to 75 mol % component X, from 20 to 55 mol% component Y and from 0.1 to 10 mol% component Z, wherein component X is $P_2O_5$, component Y is selected from ZnO, $K_2O$, $B_2O_3$ and $Al_2O_3$ in an amount of up to 20 mol% and CaO and BaO in an amount of up to 55 mol%, and component Z is selected from SrO, $Ta_2O_5$, $La_2O_3$, $CeO_2$ and $Nb_2O_5$.

DETAILED DESCRIPTION OF THE INVENTION

The chemical resistance as described above generally means durability against water or various chemical agents such as HCl, $H_2SO_4$, $HNO_3$ or etc. The materials which are superior in water resistance are in general superior in chemical resistance.

The reasons why the proportions of components X, Y and Z in the crystallized glass tooth crown material of the present invention are limited to the above-specified ranges are hereinafter described in detail.

$P_2O_5$ is a main component of phosphate glass. If the $P_2O_5$ content is less than 40 mol%, the frit is difficult to melt. On the other hand, if it is in excess of 75 mol%, the frit is unstable and lacks water resistance, and a frit quenched in water hydrates quickly.

Component Y is added to the $P_2O_5$, which is an acid component, thereby changing it from acidic to neutral, and chemically stabilizing it. If the proportion of Component Y is less than 20 mol%, the frit is unstable and poor in water resistance, and a frit quenched in water hydrates quickly. On the other hand, if it is in excess of 55 mol%, the frit is difficult to melt and cannot exhibit the desired effects.

It has also been found according to the present invention that component Z bonds to sites of the $P_2O_5$-base glass which readily adsorb a hydroxyl group(—OH), and serve to stabilize the glass by which not only water resistance but also chemical resistance are increased. If the proportion of component Z is less than 0.1 mol%, the desired effect cannot be obtained. On the other hand, if it is in excess of 10 mol%, the water resistance tends to be reduced.

The preferred embodiment of the present invention is a crystallized glass tooth crown material consisting essentially of from 40 to 60 mol% component X, from 40 to 55 mol% component Y and from 1 to 8 mol% component Z, wherein component X is $P_2O_5$, component Y is selected from ZnO, $K_2O$, $B_2O_3$ and $Al_2O_3$ in an amount of up to 20 mol% and CaO and BaO in an amount of up to 50 mol%, and component Z is selected from SrO, $Ta_2O_5$, $La_2O_3$, $CeO_2$ and $Nb_2O_5$.

The more preferred embodiment of the present invention is a crystallized glass tooth crown material consisting essentially of from 40 to 60 mol% component X, from 40 to 55 mol% component Y and from 1 to 8 mol% component Z, wherein component X is $P_2O_5$, component Y is selected from $K_2O$ and $B_2O_3$ in amount of up to 20 mol% and CaO and BaO in an amount of up to 50 mol%, and component Z is selected from SrO, $La_2O_3$ and $CeO_2$.

For component Y, $K_2O$, $B_2O_3$, CaO and/or BaO are preferred because of providing good affinity for living body.

For component Z, SrO, $La_2O_3$ and/or $CeO_2$ are also preferred because of providing good affinity for living body.

Lost wax process as well known in the field of dentistry can be applied to the production of the crystallized glass tooth crown material of the present invention.

A process for the production of the crystallized glass tooth crown material of the present invention is described below.

For component X, in addition to orthophosphoric acid ($H_3PO_4$), ammonium secondary phosphate (($NH_4)_2HPO_4$) and ammonium tertiary phosphate (($NH_4)_3PO_4$) can be used.

For component Y, in addition to directly using the oxides ZnO, $K_2O$, $B_2O_3$, $Al_2O_3$, CaO, and BaO, the carbonates and hydroxides of the respective metals, which are converted into the above oxides upon heating, can be used. In addition, the metals may be used in the form of compounds in combination with phosphoric acid, the examples of which compounds include $Ca_3(PO_4)_2$, $Zn_3(PO_4)_2$, $AlPO_4$, $K_3PO_4$ and $Ba_3(PO_4)_2$.

For component Z, analogously to component Y, the oxides SrO, $Ta_2O_5$, $La_2O_3$, $CeO_2$, and $Nb_2O_5$ may be used directly in the oxide form, or as the carbonates and hydroxides of the respective metals can be used, or use can be in the form of compounds of the metals in combination with phosphoric acid.

The above starting materials are pulverized and mixed in a mixer such as a trommel, mixer-blender, etc., melted at 1,000° C. to 1,200° C in a crucible made of a refractory substance, such as alumina, mullite, or platinum, poured into a metallic mold maintained at 600° C. to 700° C., molded into a form of tooth crown while at the same time cooling quicly and glassifying, raised in temperature to a temperature 50° C. higher than the crystallization temperature at a temperature-raising rate of from 50° C. to 200° C./hr, maintaining the material at that temperature for from 1 to 3 hours, and then cooling at a cooling rate of from 50° C. to 300° C./hr. Thus there is produced a crystallized glass tooth crown material, which has a milk white color closely approximating that of human teeth.

The present invention is described in greater detail with reference to the following example.

EXAMPLE $H_3PO_4$, $BaCO_3$, $CaCO_3$, $MgCO_3$, ZnO, $H_3BO_3$, $Al_2O_3$, SrO, $Ta_2O_5$, $La_2O_3$, $CeO_2$ and $Nb_2O_5$ were weighed out to form compositions as shown in Table 1 at the time of formation of the frit, and mixed, melted at 1,000° C. to 1,200° C. in a platinum crucible, poured into a metallic mold, and molded into the form of a tooth crown while at the same time quickly cooling with water and glassifying. Then the tooth crown materials were raised in temperature to a temperature 50° C. higher than their crystallization temperatures as indicated in Table 1 at a rate of 100° C./hr, maintained at that temperature for 2 hours, and then cooled to room temperature at a rate of 100° C./hr, whereupon crystallized glassed AR to M were produced. Crystallized glass materials AR and IR are comparative products, and the others are the products of the present invention.

The characteristics of the above crystallized glass tooth crown materials are shown in Table 1.

TABLE 1

| Crystallized Glass Tooth Crown Material | Composition (mol %) | | | | | | Transition Point (°C.) | Coefficient of Linear Thermal Expansion (30–400° C.) (/°C.) | Crystallization Temperature (°C.) | Remarks |
|---|---|---|---|---|---|---|---|---|---|---|
| | Component X mol % | | Component Y mol % | | Component Z mol % | | | | | |
| AR | $P_2O_5$ | 47 | CaO<br>$Al_2O_3$<br>BaO | 44<br>1<br>8 | | 0 | 506 | $108 \times 10^{-7}$ | 666 | Comparative example |
| B | $P_2O_5$ | 47 | CaO<br>$Al_2O_3$<br>BaO | 44<br>1<br>5 | SrO | 3 | 520 | $118 \times 10^{-7}$ | 690 | Example of this invention |
| C | $P_2O_5$ | 47 | BaO | 5 | $Ta_2O_5$ | 3 | 532 | $104 \times 10^{-7}$ | 700 | Example of this invention |
| D | $P_2O_5$ | 47 | BaO | 5 | $La_2O_3$ | 3 | 530 | $116 \times 10^{-7}$ | 678 | Example of this invention |
| E | $P_2O_5$ | 47 | BaO | 5 | $CeO_2$ | 3 | 524 | $110 \times 10^{-7}$ | 690 | Example of this invention |
| F | $P_2O_5$ | 47 | BaO | 5 | $Nb_2O_5$ | 3 | 532 | $94 \times 10^{-7}$ | — | Example of this invention |
| G | $P_2O_5$ | 47 | BaO | 5 | SrO | 6 | 500 | $125 \times 10^{-7}$ | 650 | Example of this invention |
| H | $P_2O_5$ | 47 | BaO | 5 | SrO | 8 | 470 | $140 \times 10^{-7}$ | 620 | Example of this invention |
| IR | $P_2O_5$ | 47 | BaO | 5 | SrO | 15 | 450 | $160 \times 10^{-7}$ | 600 | Comparative example |
| J | $P_2O_5$ | 46 | BaO<br>$Al_2O_3$<br>MgO | 44<br>2<br>5 | SrO | 3 | 500 | $150 \times 10^{-7}$ | 710 | Example of this invention |
| K | $P_2O_5$ | 60 | CaO<br>BaO<br>$Al_2O_3$<br>ZnO<br>MgO<br>$K_2O$ | 5<br>10<br>7<br>5<br>5<br>5 | SrO | 3 | 498 | $110 \times 10^{-7}$ | 715 | Example of this invention |
| L | $P_2O_5$ | 70 | CaO<br>$Al_2O_3$<br>MgO<br>$B_2O_3$ | 5<br>7<br>5<br>10 | SrO | 3 | 560 | $93 \times 10^{-7}$ | 760 | Example of this invention |
| M | $P_2O_5$ | 60 | BaO<br>ZnO | 20<br>17 | SrO | 3 | 543 | $105 \times 10^{-7}$ | 720 | Example of this invention |

The above-produced crystallized glass tooth crown materials were allowed to stand in an atmosphere at 60° C. and 95% RH (relative humidity), and the time until discoloration occurred was measured. The results are shown in Table 2.

TABLE 2

| Crystallized Glass Tooth Crown Material | Time taken for Discoloration to occur (hours) | Remarks |
|---|---|---|
| AR | 300 | Comparative example |
| B | more than 1,000 | Example of this invention |
| C | more than 1,000 | Example of this invention |
| D | 900 | Example of this invention |
| E | 800 | Example of this invention |
| F | 600 | Example of this invention |
| G | more than 1,000 | Example of this invention |
| H | more than 1,000 | Example of this invention |
| IR | 500 | Comparative example |
| J | 900 | Example of this |

TABLE 2-continued

| Crystallized Glass Tooth Crown Material | Time taken for Discoloration to occur (hours) | Remarks |
| --- | --- | --- |
| K | 800 | Example of this invention |
| L | 650 | Example of this invention |
| M | 700 | Example of this invention |

The coefficient of linear thermal expansion of the crystallized glass tooth crown material of the present invention is near that of the enamel of the human teeth (i.e., $11.4 \times 10^{-6}/°C.$ (30-400° C.)). For this reason, the difference in expansion between the crystallized glass tooth crown material and human teeth is small. Thus the crystallized glass tooth crown material of the present invention is excellent in matching the expansions and contractions of tooth enamel which it may contact.

It can be seen from Table 2 that the crystallized glass tooth crown material of the present invention is superior in moisture resistance to the comparative glasses.

While the invention has been described in detail and with reference to specific embodiments thereof, it will be apparent to one skilled in the art that various changes and modifications can be made therein without departing from the spirit and scope thereof.

What is claimed is:

1. A crystallized glass tooth crown consisting essentially of from 40 to 75 mol% component X, from 20 to 55 mol% component Y and from 0.1 to 10 mol% component Z, wherein
   component X is $P_2O_5$,
   component Y is selected from ZnO, $K_2O$, $B_2O_3$, and $Al_2O_3$ in an amount of up to 20 mol% and additionally CaO and BaO in an amount to bring the total mol% of component Y to up to 55 mol%, and
   component Z is selected from SrO, $Ta_2O_5$, $La_2O_3$, $CeO_2$ and $Nb_2O_5$.

2. A crystallized glass tooth crown as claimed in claim 1, wherein said component X is in an amount of 40 to 60 mol%.

3. A crystallized glass tooth crown as claimed in claim 1, wherein said component Y is in an amount of 44 to 55 mol%.

4. A crystallized glass tooth crown as claimed in claim 1, wherein said component Z is in an amount of 1 to 8 mol%.

5. A crystallized glass tooth crown as claimed in claim 1, wherein said component Y is selected from ZnO, $K_2O$, $B_2O_3$ and $Al_2O_3$ in an amount of up to 20 mol% and additionally CaO and BaO in an amount to bring the total mol% of component Y to up to 50 mol%.

6. A crystallized glass tooth crown as claimed in claim 1, wherein said component Y is selected from $K_2O$ and $B_2O_3$ in an amount of up to 20 mol% and additionally CaO and BaO in an amount to bring the total mol% of component Y to up to 55 mol%.

7. A crystallized glass tooth crown as claimed in claim 1, wherein said component Z is selected from SrO, $La_2O_3$ and $CeO_2$.

* * * * *